United States Patent
Ito

(10) Patent No.: US 6,409,666 B1
(45) Date of Patent: Jun. 25, 2002

(54) TIP END OF ULTRASONIC ENDOSCOPE

(75) Inventor: Keiji Ito, Saitama-ken (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/548,323

(22) Filed: Apr. 12, 2000

(30) Foreign Application Priority Data

Apr. 15, 1999 (JP) .......................................... 11-108083
Apr. 15, 1999 (JP) .......................................... 11-108084

(51) Int. Cl.[7] ............................................... A61B 8/12
(52) U.S. Cl. ...................................... 600/439; 600/463
(58) Field of Search ................................. 600/437, 439, 600/459, 461–463, 466–467, 471

(56) References Cited

U.S. PATENT DOCUMENTS

| | | | | |
|---|---|---|---|---|
| 4,605,009 A | * | 8/1986 | Pourcelot et al. | 600/463 |
| 4,759,372 A | * | 7/1988 | Umemura et al. | 600/447 |
| 4,763,662 A | * | 8/1988 | Yokoi | 600/463 |
| 5,471,988 A | * | 12/1995 | Fujio et al. | 600/439 |
| 5,492,126 A | * | 2/1996 | Hennige et al. | 600/439 |
| 5,499,630 A | * | 3/1996 | Hiki et al. | 600/461 |
| 5,853,368 A | * | 12/1998 | Solomon et al. | 600/439 |
| 6,149,598 A | * | 11/2000 | Tanaka | 600/462 |
| 6,171,249 B1 | * | 1/2001 | Chin et al. | 600/461 |

* cited by examiner

Primary Examiner—Francis J. Jaworski
(74) Attorney, Agent, or Firm—Greenblum & Bernstein, P.L.C.

(57) ABSTRACT

A flexible insertion tube of an endoscope includes a bendable portion that is formed at a tip end portion thereof. The bendable portion is formed to be bendable in an arbitrary direction. A tip end main body is connected at the tip end of the bendable portion. The tip end main body is provided with an ultrasonic scanning unit and an observation unit. The tip end main body includes a tip end side portion and a rear end side portion. The tip end side portion is provided with a convex type ultrasonic probe, and the rear end side portion is provided with: an instrument outlet allowing a treatment instrument to protrude, which is located at a central portion on a cross section of the rear end side portion; an observation window, which is directed to a forward side with respect to a scanning direction of the ultrasonic probe, and an illumination window for emitting light to illuminate an area to be observed through the observation window. The observation window is located, on one side of the instrument outlet; and the illumination window is located on the other side of the instrument outlet.

10 Claims, 7 Drawing Sheets

TIP END OF ULTRASONIC ENDOSCOPE

BACKGROUND OF THE INVENTION

The present invention relates to an ultrasonic endoscope, an end portion of which is inserted in bronchial tubes with optical observation to obtain ultrasonic sectional images of slices thereof.

Conventionally, ultrasonic endoscopes have been utilized. Most of the ultrasonic endoscopes are used for digestive tubes. Such endoscopes are constructed such that a bendable portion is formed at a distal end portion of a flexible insertion tube. The bendable portion is generally formed to bend in arbitrary direction by the operation of the proximal end side thereof. Further, an end side main body, which is provided with an ultrasonic scanning unit and an optical observing unit, is connected to the tip end of the bendable portion.

The optical observing unit is formed with a pair of forward-inclined surfaces, one of which is provided with a treatment instrument projection groove, and the other of which is provided with an observing window and an illuminating window. In the treatment instrument projection groove, a rockable table which is remotely operated to rock for adjusting the projecting direction of the treatment instrument, is provided.

An objective optical system for optical observation is preferably configured to view an inclined area with respect to the forward direction of the insertion tube so that a portion to which the ultrasonic scanning is applied, and the optical axis of the objective optical system is preferably inclined by 45–60 degrees with respect to the forward direction of the insertion portion.

The ultrasonic endoscope as described above cannot be inserted in the bronchial tubes, since its outer diameter is too large. However, it is difficult to reduce the outer diameter of such an insertion tube in view of its mechanical strength/structure.

Further, in the conventional ultrasonic endoscopes, observing characteristics thereof may not be appropriate for observing the bronchial tubes, and the insertion tube may be inserted half-blindly. In such a case, if mucosae of the bronchial tube is strongly rubbed, a patient may have a fit of coughing, and investigation may be disturbed.

Furthermore, one of the purposes to insert the ultrasonic endoscope in a bronchial tube is to execute the centesis using a centesis needle with monitoring the ultrasonic cross sectional images of lymph nodes around the bronchial tubes.

The lymph nodes are located at positions apart from the wall of the bronchial tube by 2 mm at the closest, and 10 through 15 mm for farther ones. When the conventional ultrasonic endoscope is used for the centesis, the lymph nodes relatively far from the wall of the bronchial tube may be out of a range of the ultrasonic scanning, and thus, the position of the lymph nodes cannot be determined accurately.

SUMMARY OF THE INVENTION

It is therefore an object of the invention to provide an improved tip end of an ultrasonic endoscope which can be used in bronchial tubes with allowing optical observation thereof.

Another object of the invention is to provide an improved tip end of an ultrasonic endoscope which enables monitoring of the ultrasonic images of lymph nodes even if they are apart from the wall of the bronchial tube and allows the centesis operation to be performed safely.

For the above object, according to an aspect of the invention, there is provided a tip end portion of an ultrasonic endoscope having a flexible insertion tube, a bendable portion being formed at a tip end portion of the insertion tube, the bendable portion being bendable in an arbitrary direction along a predetermined plane, a tip end main body provided with an ultrasonic scanning unit and an observation unit being connected to a tip end of the bendable portion, the tip end main body having a tip end side portion and a rear end side portion. The tip end side portion of the main body is provided with a convex type ultrasonic probe for performing sector scanning with ultrasonic waves, and the rear end side portion of the main body being provided with: an instrument outlet allowing a treatment instrument to protrude toward a forward-inclined direction, the outlet being located at a central portion on a cross section of the rear end side portion; an observation window for viewing forward-inclined area which is directed to a forward side with respect to a scanning direction of the ultrasonic probe, the observation window being located, on one side of the instrument outlet; and an illumination window for emitting and illuminating an area to be observed through the observation window, on the other side of the instrument outlet.

With the above structure, the tip end of the ultrasonic endoscope can be made sufficiently slim, and accordingly, can be inserted in the bronchial tubes easily. Further, the forward portion of the inserted tip end can be optically observed, which also enables a smooth movement inside the bronchial tube.

Optionally, a protruding direction of the treatment instrument may be directed toward a forward side with respect to a scanning direction of said ultrasonic probe.

Further optionally, an axis of observation through the observation window may be inclined at an angle within 5° through 45° with respect to a forward direction of the insertion portion.

Still optionally, the center of the scanning direction of the ultrasonic probe may be formed to incline by 75° through 90° with respect to the forward direction of the insertion tube.

Furthermore, the surface of the ultrasonic probe may be a spheric convex surface, a radius of curvature of which being within a range of 5 through 15 mm.

Further optionally, the tip end of the endoscope may be provided with a pair of signal transmitting cables for transmitting/receiving electrical signals to/from the ultrasonic scanning unit. The cables may extend along the insertion tube and be aligned side-by-side.

According to another aspect of the invention, there is provided a tip end portion of an ultrasonic endoscope having a flexible insertion tube, a tip end main body provided with an ultrasonic scanning unit and an observation unit being connected to a tip end of the insertion tube, the tip end main body having a tip end side portion and a rear end side portion. The tip end side portion of the main body is provided with a convex type ultrasonic probe for performing sector scanning with ultrasonic waves, and the rear end side portion of the main body is provided with: an instrument outlet allowing a treatment instrument to protrude toward a forward-inclined direction, a protruding direction of the treatment instrument being directed toward a forward side with respect to a scanning direction by the ultrasonic scanning direction; and an observation window for viewing forward-inclined area which is directed to a forward side with respect to the protruding direction of the treatment instrument.

With this structure, the ultrasonic probe can be inserted with monitoring the optical image of the forward portion thereof, and the centesis operation can be done safely since the lymph nodes, whether they are apart from or close to the wall of the bronchial tube, may remain within a range of the ultrasonic scanning.

Optionally, the center of the scanning direction of the ultrasonic probe may be formed to incline by 75° through 90° with respect to the forward direction of the insertion tube.

Further, the surface of the ultrasonic probe may be a spheric convex surface, a radius of curvature of which being within a range of 5 through 15 mm.

Furthermore, an axis of observation through the observation window may be inclined at an angle within 5° through 45° with respect to a forward direction of the insertion portion.

BRIEF DESCRIPTION OF THE ACCOMPANYING DRAWINGS

Figure 7:
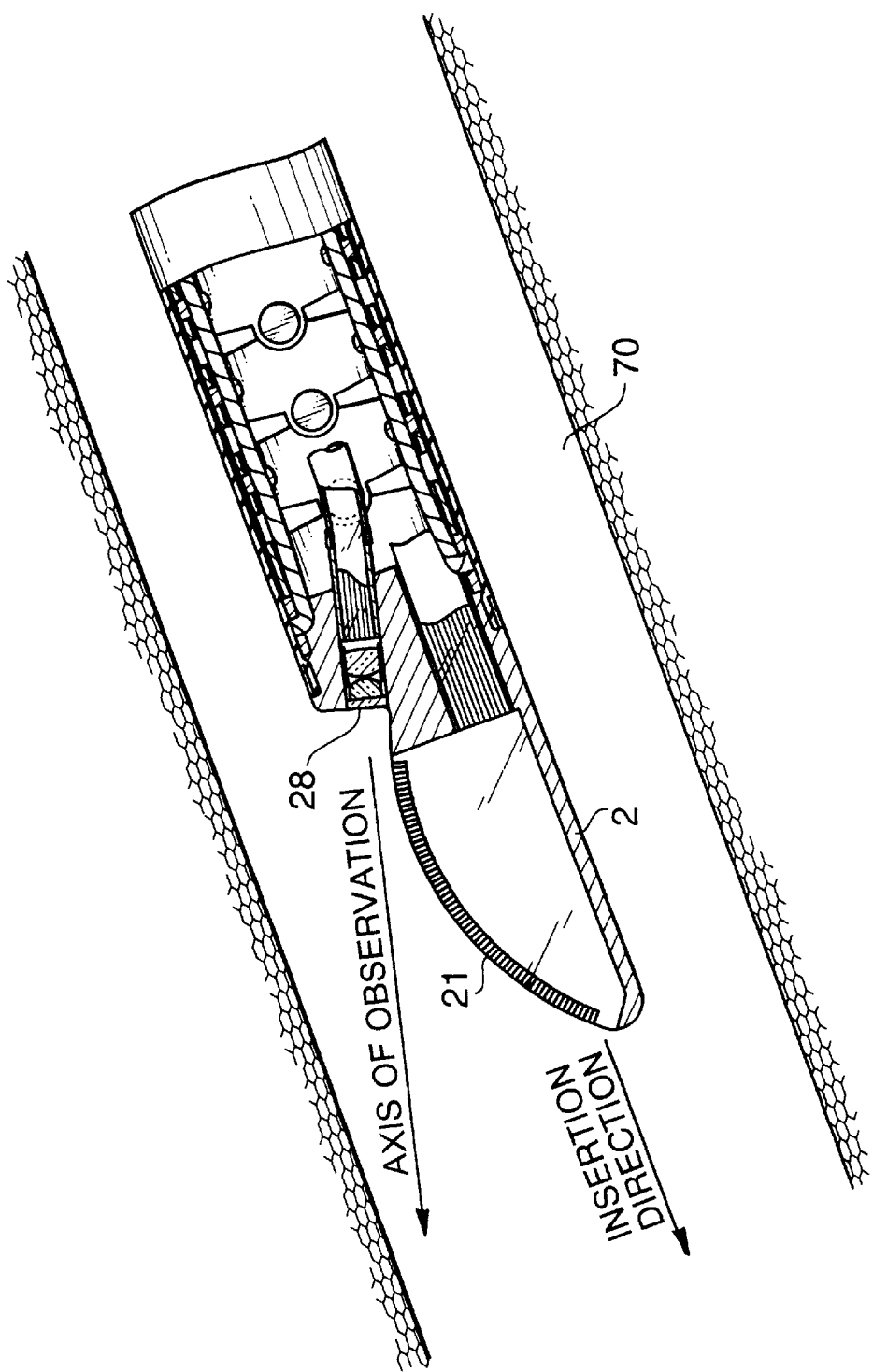
Figure 8:
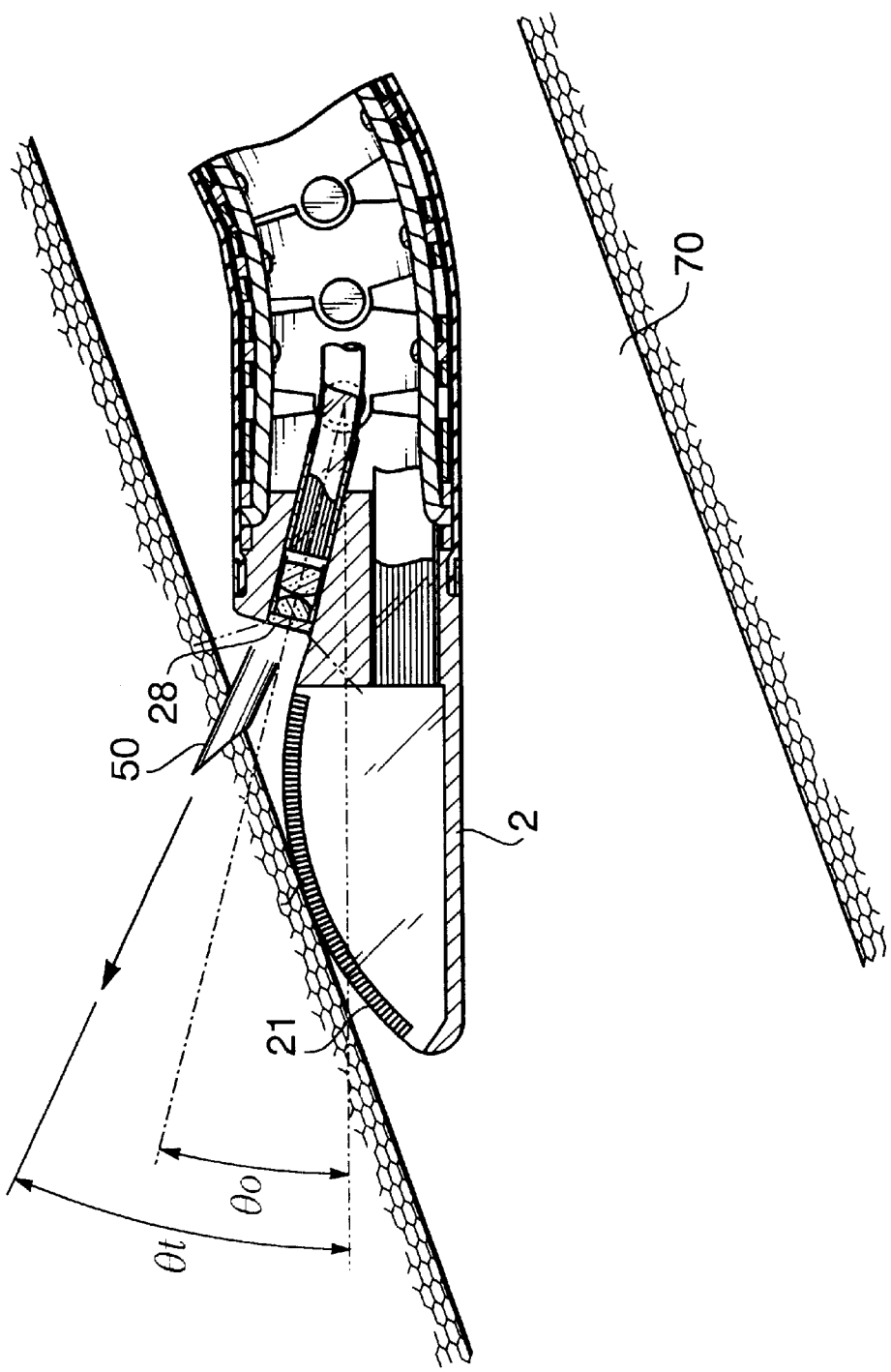
Figure 9:
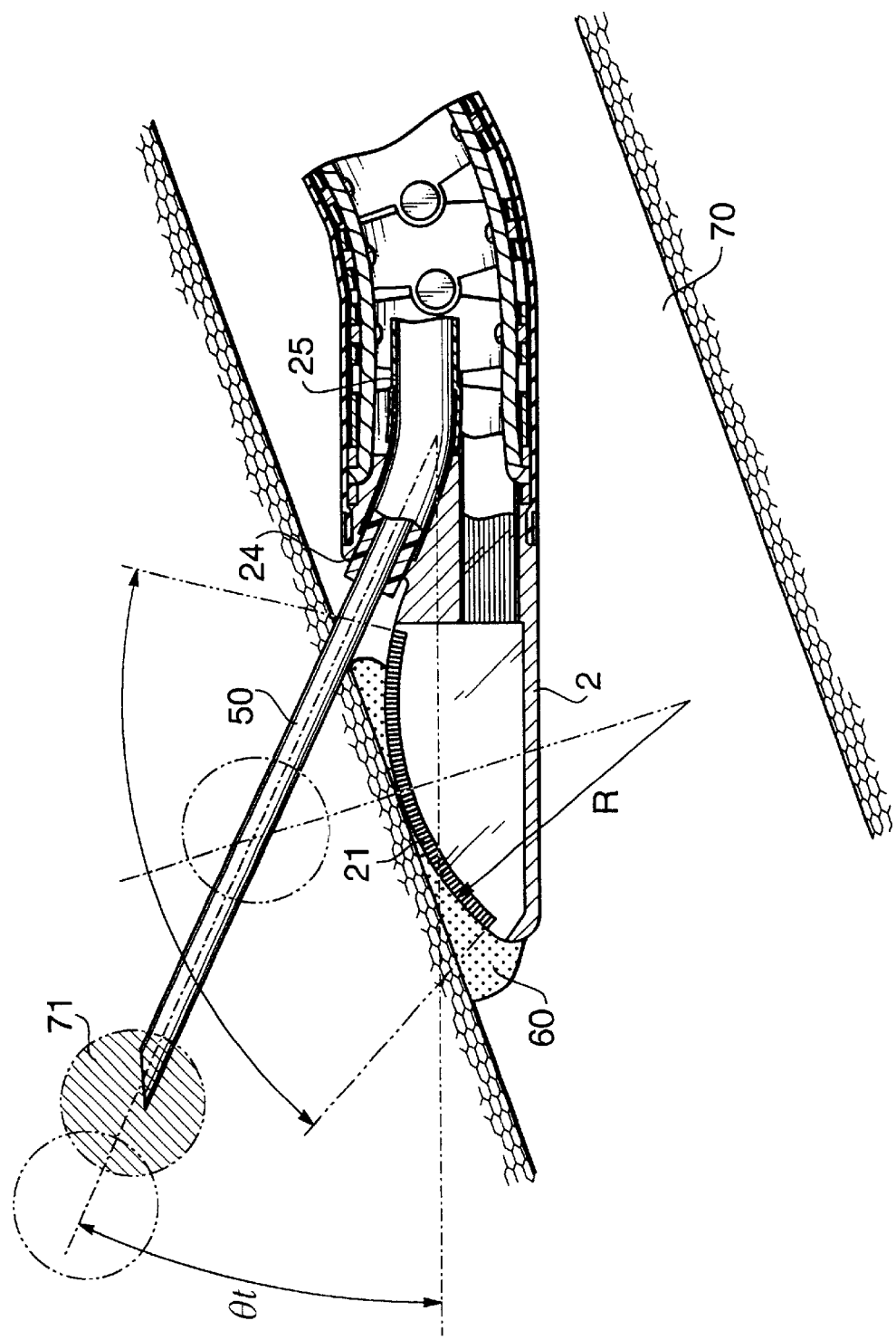

FIG. 7 schematically shows a cross sectional view of the tip end portion of the ultrasonic endoscope when inserted in a bronchial tube;

FIG. 8 schematically shows a cross sectional view of the tip end portion of the ultrasonic endoscope when inserted in a bronchial tube; and FIG. 9 schematically shows a cross sectional view of the tip end portion of the ultrasonic endoscope when inserted in a bronchial tube and a centesis operation is performed.

DETAILED DESCRIPTION OF THE EMBODIMENT

Hereinafter, an embodiment of the present invention will be described with reference to the accompanying drawings.

Figure 1:
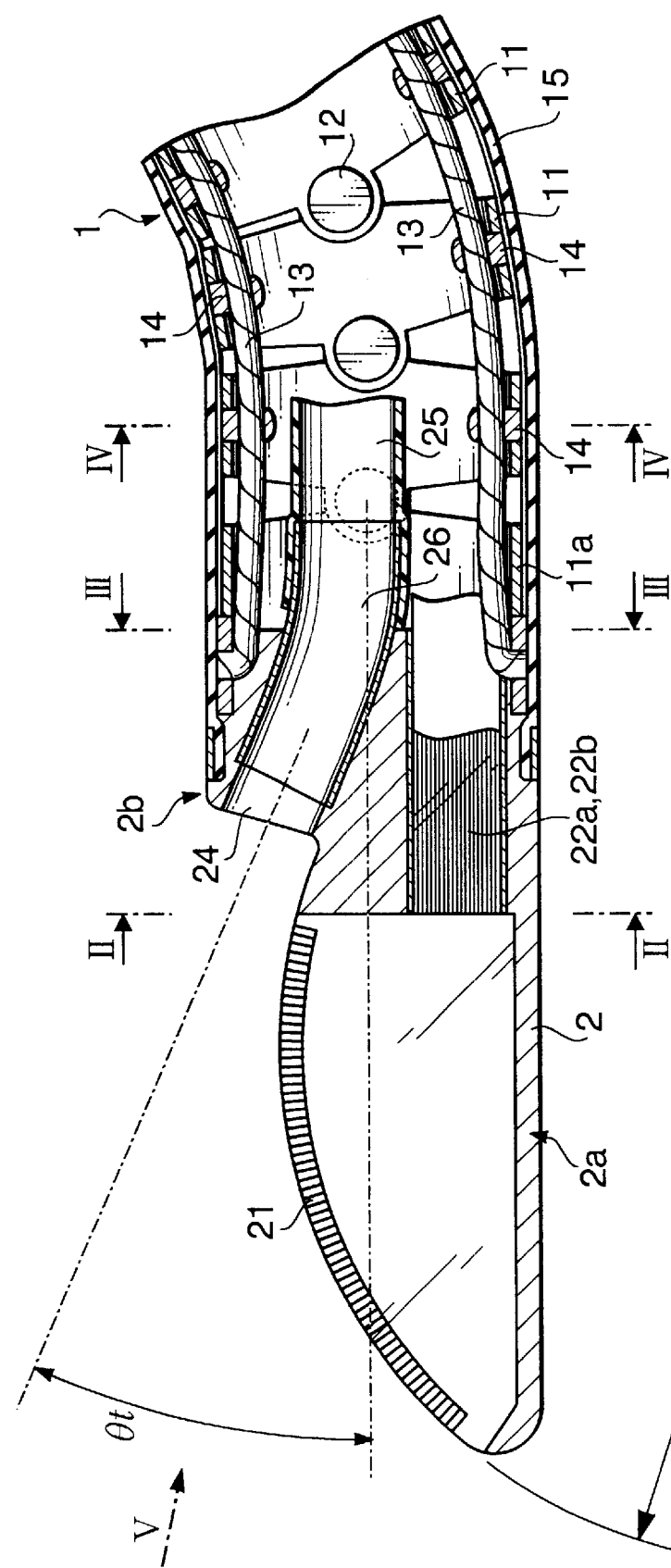
FIG. 1 is a cross sectional side view of a tip end portion of a ultrasonic endoscope according to an embodiment of the present invention.

FIG. 1 is a cross sectional view of a tip end portion of an ultrasonic endoscope according to an embodiment of the invention. The endoscope has a flexible insertion tube, at the tip end portion of the flexible insertion tube, a bendable portion 1 is formed.

The bendable portion 1 includes a plurality of, e. g., from five through fifteen, ring members 11 which are sequentially connected with rivets so as to rotate, about the rivets, with respect to each other. To the ring member 11a at the extreme end of the connected ring members, ends of a pair of upper and lower operation wires 13, which are draw-operated at an operation unit (not shown) connected to the proximal end of the insertion tube so that a bending angle of the bendable portion 1 is changed arbitrarily.

It should be noted that in this embodiment, all the ring members 11 incline in the same direction, and therefore, the bendable portion 1 is bendable along a plane which is parallel with a surface of FIG. 1. That is, in this embodiment, the bendable portion 1 is bendable in the upper and lower direction in FIG. 1. On the inner surface, at the upper and lower portions, of each ring member 11, a wire guide 14 for guiding the operation wire 13 is protruded inwardly. The outer surface of the bendable portion 1 is covered with a sheath 15 which is an elastic tube made of rubber.

A tip end main body 2 is connected to the distal end of the bendable portion 1. A front side half of the tip end main body 2 is an ultrasonic scanning unit 2a, and a rear side half thereof is an observation unit 2b.

The ultrasonic scanning unit 2a is provided with an ultrasonic probe 21 of a so-called convex type. The tip end portion 2 where the ultrasonic probe 21 is provided is formed, when viewed from a side, a convex shape, e.g., an arc-shaped portion whose radius is 10 millimeters, and a plurality of ultrasonic wave receiving elements are arranged on the arc shaped portion.

Figure 6:
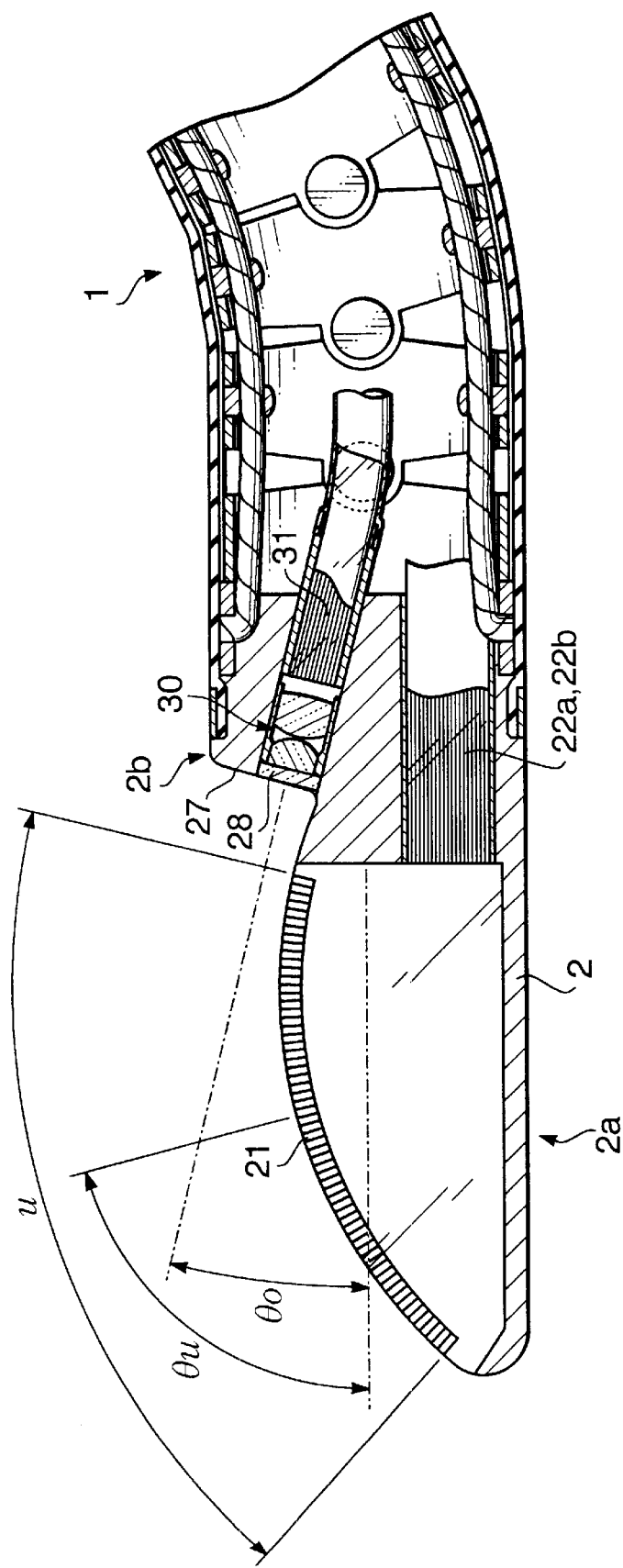
FIG. 6 is a cross sectional view of the tip end portion of the ultrasonic endoscope taken along line VI—VI in FIG. 5.

A sector scanning is performed with the ultrasonic probe 21. The central axis of the ultrasonic probe 21 is inclined upwardly with respect to the forward direction of the tip end portion 2 by 75–90 degrees. For example, as shown in FIG. 6, within a sector area of 65 degrees, ultrasonic wave signals are transmitted/received. That is, $75° \leq \theta u \leq 90°$ and $U=65°$. Then, across sectional image of a slice of an object is displayed on a monitor device (not shown).

Figure 2:
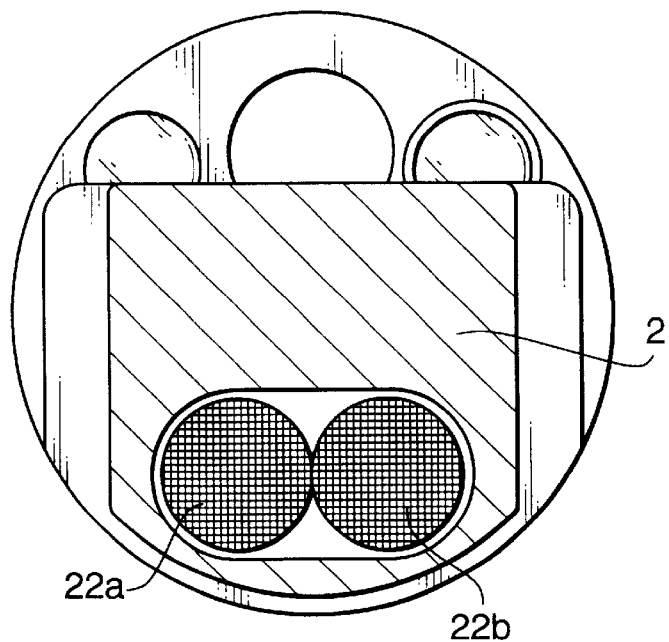
FIG. 2 is a cross sectional view of the tip end portion of the ultrasonic endoscope, taken along line II—II of FIG. 1.
Figure 3:
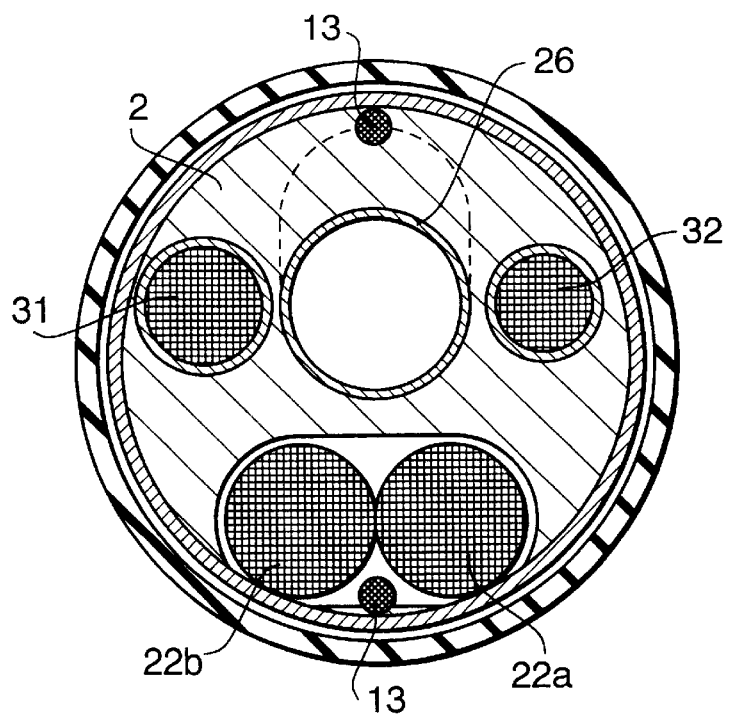
FIG. 3 is cross sectional view of the tip end portion of the ultrasonic endoscope taken along line III—III of FIG. 1.
Figure 4:
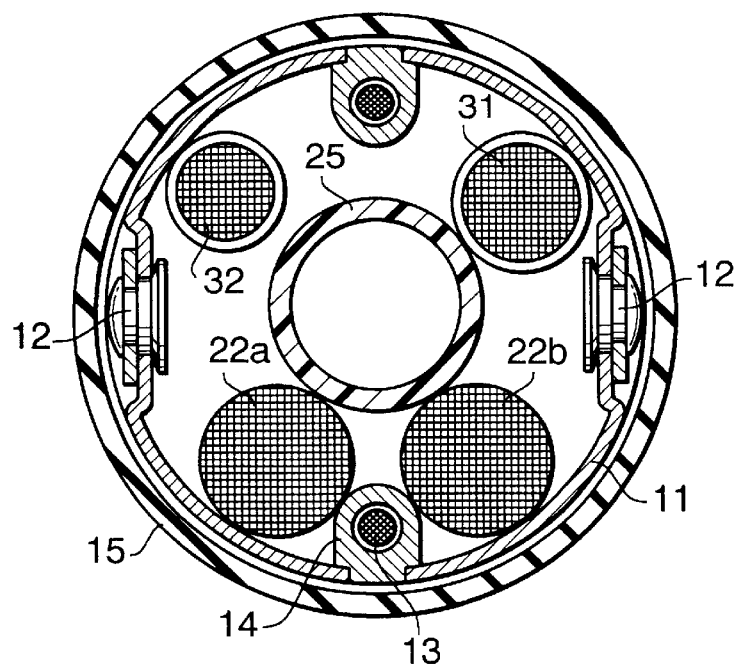
FIG. 4 is cross sectional view of the tip end portion of the ultrasonic endoscope taken along line IV—IV of FIG. 1.

Signal cables 22a and 22b extending rearward from the ultrasonic scanning unit 2a are shown in FIGS. 2, 3 and 4, which are cross sectional views of the tip end portion 2 of the ultrasonic endoscope 100, taken along line II—II, line III—III and line IV—IV of FIG. 1, respectively. The signal cables 22a and 22b are arranged side-by-side at a lower portion inside the tip end portion 2.

As shown in FIGS. 3 and 4, the lower operation wire 13 and the wire guide 14 thereof are sandwiched between the cables 22a and 22b, thus a space inside the bending portion 1 is efficiently used.

As shown in FIG. 1, at the observation unit 2b, a treatment instrument outlet 24 is formed, from which a treatment instrument is to be protruded toward a scanning surface of the ultrasonic probe 21. The central axis of the outlet 24 inclines upwardly with respect to a forward direction of the main body 2, f or example, by 25° (i.e., $\theta t=25°$). Thus, $\theta t$ is smaller than $\theta u$.

The outlet 24 communicates with a instrument channel 25, which is formed through the entire length of the insertion tube of the endo scope 100, via a connection tube 26. In order to suppress the outer diameter of the tip end portion 2, at the outlet 24, a rockable table, which is used, as aforementioned, for adjusting the protruding direction of the instrument or the like is not provided.

Figure 5:
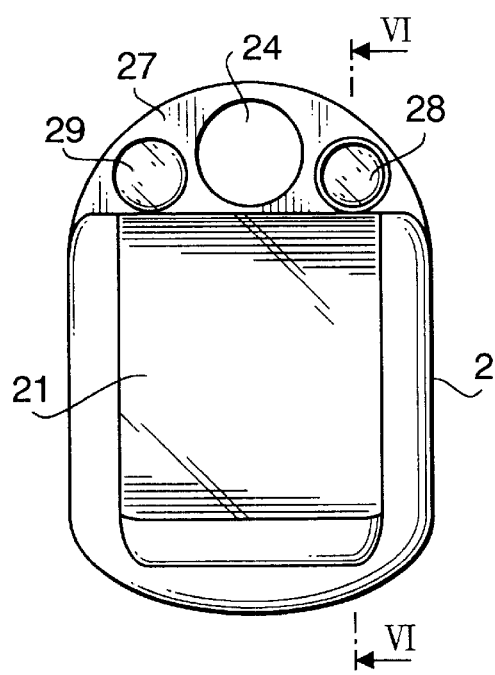
FIG. 5 is a front of the tip end of the endoscope viewed along arrow V in FIG. 1.

FIG. 5 is a front view of the tip end portion 2 viewed from arrow V in FIG. 1. As shown in FIG. 5, at a central area of an inclined surface, which is formed at an upper portion of the tip end surface the observation unit 2a, the outlet 24 is provided. On one side of the outlet 24, an observation window 28 for optically observing forward-inclined area with respect to the scanning direction of the ultrasonic probe 21, and on the other side of the outlet 24, an illumination window 29 for emitting light to illuminate an area to be observed is provided.

FIG. 6 is a cross sectional view of the tip end portion 2 of the ultrasonic endoscope 100 taken along line VI—VI in FIG. 5. It should be noted that the cross section of the bendable portion 1 is that taken along a plane including the central axis thereof as in FIG. 1.

Inside the observation window 28, an objective optical system 30 is provided. At a focal plane of the optical system 30, an end surface of an image guide fiber bundle 31 which is inserted and extending throughout the entire length of the insertion tube 1.

An axis of the observation of the objective optical system 30 inclines upward, for example by 15°, with respect to the forward direction of the tip end portion 2 (that is, θo=15°), and thus, an inclined-forward area including a surface of the ultrasonic probe 21 can be observed through an eyepiece (not shown). It should be noted that the angle θo is not limited to 15°, and may be any angle within a range of 5° through 45°. Preferably, the angle θo is within 10° through 20° if a front area is to be observed. The central axis of the illumination light emitted through the illuminating window 29 may also have the similar configuration.

FIGS. 7 and 8 schematically show cross sectional views of the tip end portion 2 of the ultrasonic endoscope 100 when inserted in a bronchial tube 70.

Since the observing axis is inclined at 15° (i.e., θo=15°) with respect to the insertion direction, as shown in FIG. 7, a portion of the bronchial tube 70 in front of the tip end main body 2 can be observed. Accordingly, the main body 2 can be inserted easily without strongly rubbing the surface of the moucosa.

As shown in FIG. 8, a centesis needle 50 is protruded from the instrument outlet 24. The centesis needle 50 is inclined at an angle of θt, which is, for example, 25°. As shown in FIG. 8, θt is greater than θo. Since θo is relatively small (i.e., θo=15°), the tip end portion of the endoscope can easily be inserted in the bronchial tube 70 with viewing the forward direction through the observing window 28. Further, since θt is relatively large (i.e., θt=25°), even if a lymph node is located at a deep part of the bronchial tube 70, The centesis needle 50 can be pushed therein with monitoring the location through the observing unit 2b. It should be noted that the centesis needle 50 can be viewed through the observation unit 2b although θt is greater than θo.

FIG. 9 schematically shows a cross sectional view of the tip end portion of the ultrasonic endoscope when inserted in a bronchial tube and a centesis operation is performed with respect to a lymph node 71 using the centesis needle 50. In order to capture a sliced image of the lymph node 71, an air layer should not exist between the ultrasonic probe 21 and the inner wall of the bronchial tube 70.

For this purpose, before inserted in the bronchial tube 70, Xylocaine jelly 60 or the like is applied on the surface of the ultrasonic probe 21. When inserted, the Xylocaine jelly 60 is filled between the inner wall of the bronchial tube 70 and the surface of the probe 21 and the air layer will not be formed therebetween.

If the radius R of curvature of the ultrasonic probe 21 is too small, both side end portions of the probe 21 may be apart from the bronchial tube 70. In such a case, even if the Xylocaine jelly 60 is applied, the air layer may be formed and the appropriate ultrasonic slice images may not be captured.

On the other hand, if the radius R of the curvature is too large, a scanning angle for the sector scanning is made too small, and it becomes difficult to extract the lymph node 71. In this case, in order to obtain a sufficient scanning range (angular range), a larger ultrasonic probe should be used. However, if a larger probe is used, it becomes difficult to insert the probe in the bronchial tube 70.

An experientially known range of the radius R of the curvature of the ultrasonic probe 21 is a range from 5 through 15 millimeters. Of course, if the probe 21 is downsized, the radius R may become a range within 2 through 3 millimeters.

The lymph node is located at positions 2 mm from the wall of the bronchial tube 70 for closer one, and 10–15 mm from the wall for farther ones. According to the embodiment described above, in view of the protruded angle of the centesis needle 50, whichever place the lymph node is located, the location of the lymph node 71 can be monitored based on the ultrasonic slice images obtained by the ultrasonic probe 21, and the centesis thereof can be performed.

The present disclosure relates to the subject matters contained in Japanese Patent Applications Nos. HEI 11-108083 and HEI 11-108084, both filed on Apr. 15, 1999, which are expressly incorporated herein by reference in their entireties.

What is claimed is:

1. A tip end portion of an ultrasonic endoscope having a flexible insertion tube, a bendable portion being formed at a tip end portion of said insertion tube, said bendable portion being bendable in an arbitrary direction along a predetermined plane, a tip end main body provided with an ultrasonic scanning unit and an observation unit being connected to a tip end of said bendable portion, said tip end main body having a tip end side portion and a rear end side portion, said tip end side portion of said main body being provided with a convex type ultrasonic probe for performing sector scanning with ultrasonic waves, said rear end side portion of said main body being provided with:

an instrument outlet allowing a treatment instrument to protrude toward a forward-inclined direction, said outlet being located at a central portion on a cross section of said rear end side portion;

an observation window for viewing forward-inclined area which is directed to a forward side with respect to a scanning direction of said ultrasonic probe, said observation window being located on one side of said instrument outlet; and an illumination window for emitting and illuminating an area to be observed through said observation window, said illumination window being located on the other side of said instrument outlet.

2. The tip end portion of the ultrasonic endoscope according to claim 1, wherein a protruding direction of the treatment instrument is directed toward a forward side with respect to a scanning direction of said ultrasonic probe.

3. The tip end portion of the ultrasonic endoscope according to claim 1, wherein an axis of observation through said observation window is inclined at an angle within 5° through 45° with respect to a forward direction of said insertion portion.

4. The tip end portion of the ultrasonic endoscope, according to claim 1, wherein the center of the scanning direction of said ultrasonic probe inclines by 75° through 90° with respect to the forward direction of said insertion tube.

5. The tip end portion of the ultrasonic endoscope according to claim 1, wherein the surface of said ultrasonic probe is a spheric convex surface, a radius of curvature of which being with in a range of 5 through 15 mm.

6. The tip end of the ultrasonic endoscope according to claim 1, further comprising signal transmitting means for transmitting/receiving electrical signals to/from said ultrasonic scanning unit, said transmitting means including a pair of cables which extending along said insertion tube and being aligned side-by-side.

7. A tip end portion of an ultrasonic endoscope having a flexible insertion tube, a tip end main body provided with an ultrasonic scanning unit and an observation unit being connected to a tip end of said insertion tube, said tip end main body having a tip end side portion and a rear end side portion, said tip end side portion of said main body being provided with a convex type ultrasonic probe for performing sector scanning with ultrasonic waves, said rear end side portion of said main body being provided with:

an instrument outlet allowing a treatment instrument to protrude toward a forward-inclined direction, a protruding direction of the treatment instrument being directed toward a forward side with respect to a scanning direction of said ultrasonic probe, said outlet being located at a central portion on a cross section of said rear end side portion;

an observation window for viewing forward-inclined area which is directed to a forward side with respect to the protruding direction of said treatment instrument, said observation window being located on one side of said instrument outlet; and an illumination window for emitting and illuminating an area to be observed through said observation window, said illumination window being located on the other side of said instrument outlet.

8. The tip end portion of the ultrasonic endoscope, according to claim 7, wherein the center of the scanning direction of said ultrasonic probe inclines by 75° through 90° with respect to the forward direction of said insertion tube.

9. The tip end portion of the ultrasonic endoscope according to claim 7, wherein the surface of said ultrasonic probe is a spheric convex surface, a radius of curvature of which being within a range of 5 through 15 mm.

10. The tip end portion of the ultrasonic endoscope according to claim 7, wherein an axis of observation through said observation window is inclined at an angle within 5° through 45° with respect to a forward direction of said insertion portion.

* * * * *